(12) United States Patent
Stillman (10) Patent No.: US 11,109,624 B2
(45) Date of Patent: Sep. 7, 2021

(54) SANITARY FINGER COVERS AND DISPENSER

(71) Applicant: Richard Irving Stillman, Mountain Lakes, NJ (US)

(72) Inventor: Richard Irving Stillman, Mountain Lakes, NJ (US)

( * ) Notice: Subject to any disclaimer, the term of this patent is extended or adjusted under 35 U.S.C. 154(b) by 0 days.

(21) Appl. No.: 16/850,332

(22) Filed: Apr. 16, 2020

(65) Prior Publication Data

US 2021/0195970 A1  Jul. 1, 2021

Related U.S. Application Data

(60) Provisional application No. 62/956,292, filed on Jan. 1, 2020.

(51) Int. Cl.
| | |
|---|---|
| *A61B 42/40* | (2016.01) |
| *A41D 13/08* | (2006.01) |
| *A61L 2/10* | (2006.01) |
| *A61B 42/50* | (2016.01) |

(52) U.S. Cl.
CPC ............ *A41D 13/087* (2013.01); *A61B 42/40* (2016.02); *A61L 2/10* (2013.01); *A61B 42/50* (2016.02)

(58) Field of Classification Search
CPC ............ A61B 42/40; A61B 42/50; A61L 2/10; A41D 13/087
USPC .......................................................... 221/45
See application file for complete search history.

(56) References Cited

U.S. PATENT DOCUMENTS

| | | | | |
|---|---|---|---|---|
| 3,067,001 A * | 12/1962 | McCollum | ............ | A61B 42/00 422/28 |
| 3,902,509 A * | 9/1975 | Tundermann | .......... | A61C 15/02 433/142 |
| 5,604,952 A * | 2/1997 | Zeleznick | ................ | A46B 3/18 15/167.1 |
| 6,179,159 B1 * | 1/2001 | Gurley | ................... | A61B 42/20 206/278 |
| 6,243,868 B1 * | 6/2001 | Wanzenried | ......... | A41D 13/087 2/21 |
| 8,678,252 B2 * | 3/2014 | Kelly | ..................... | A61B 42/40 223/111 |
| 8,807,402 B2 * | 8/2014 | Backhaus | .......... | A41D 19/0072 223/111 |
| 9,723,879 B1 | 8/2017 | Delgrosso | | |
| 10,098,699 B1 * | 10/2018 | Buck | ...................... | A61B 90/90 |
| 10,610,319 B2 * | 4/2020 | Backhaus | ............ | A47G 25/904 |
| 2008/0000011 A1 | 1/2008 | Ayala | | |
| 2010/0088794 A1 | 4/2010 | Oradini, Sr. | | |
| 2013/0025016 A1 | 1/2013 | Koffi et al. | | |
| 2018/0085179 A1 * | 3/2018 | Ju | .......................... | A61B 42/50 |

* cited by examiner

*Primary Examiner* — Patrick H Mackey
(74) *Attorney, Agent, or Firm* — H. Jay Spiegel (57) ABSTRACT

A dispenser of sanitary finger covers which are sanitized individually at the time of use. The system uses either a battery operated ultraviolet LED or spray disinfectant to automatically or manually sanitize the finger covers. The sanitary finger covers can be rapidly applied without contamination using a single finger. Removal and disposal are similarly rapid and easy. The finger covers are inexpensive and may be made from a variety of readily available and biodegradable materials. The dispenser is lightweight and portable. It can be carried by the user or attached to their uniform. The dispenser can be easily replenished with finger covers once empty, using a provided cartridge prefilled with finger covers.

12 Claims, 7 Drawing Sheets

SANITARY FINGER COVERS AND DISPENSER

The present invention relates to sanitary finger covers and embodiments of a dispenser to dispense them. The field of endeavor of the present invention includes infection control and devices which prevent transmission of infection, such as gloves. Applicant claims priority from provisional application Ser. No. 62/956,292, filed Jan. 1, 2020.

BACKGROUND OF THE INVENTION

The COVID-19 pandemic has created heightened awareness about the surfaces we contact with our hands and the subsequent touching of one's face with potentially virus-laden hands. It has been shown that coronaviruses, as well other infectious microbial agents involved in epidemics, remain viable and transmissible on many surfaces for a significant period of time.

This problem is particularly of concern to the restaurant industry, since waiters generally serve plates of food using their bare hands. In most cases, the thumb grasps the top surface of the plate containing food while the other four fingers support the undersurface of the plate. This creates a potential source of transmission of infectious agents from the waiter's fingers, particularly the thumb, to the consumer of the food on the plate. Additionally, removing a used plate in this fashion after a meal potentially exposes the waiter's fingers to the patron's oral secretions left on the plate. This cycle of serving and removing plates is repeated over and over again, from customer to customer, amplifying the risk of transmission of disease.

The National Outbreak Reporting System (NORS) at the Center for Disease Control (CDC) has documented over 46,000 outbreaks of food-born illnesses since 1998, involving well over one million individuals, causing 31,000 hospitalizations and 1,500 deaths. Many different microbial species, both bacterial and viral, have been identified as the infectious agents in these outbreaks. Food handlers, including servers, have been implicated in a significant proportion of these outbreaks. Often, a food-worker may be contagious and shed these infectious microbes onto their own fingertips several days before becoming symptomatic. This makes identification and isolation of the infectious individual difficult. While the current coronavirus pandemic has become the primary focus, many other pathogens are also problematic. Most recently, a single asymptomatic food handler with Hepatitis A was implicated in the infection of 17 persons, including one death, at The Mendham Country Club in New Jersey in 2019.

The CDC and health departments across the country have promulgated guidelines and recommendations addressing this problem. Central to these recommendations is regular and meticulous hand washing as well as usage of gloves when food handlers are in direct contact with food or serving plates. However, both of these interventions have been documented to have low compliance rates. Additionally, studies have shown that gloved hands quickly become contaminated during use when the user inadvertently touches their nose, mouth or any other contaminated surface such as a used food plate.

Given the fear associated with the current pandemic, the revitalization of the restaurant industry will largely depend upon the public's confidence in the food they are served.

The present invention is intended to solve this problem by providing a novel device, method and system for rapidly dispensing sanitary finger covers, which have been sanitized immediately prior to application by the user.

The following prior art is known to Applicant:

U.S. Published Application No. US 2010/0088794 A1 to Oradini, Sr. (Oradini) discloses sanitary finger covers, a dispenser for the covers and a method for applying the covers. The covers described are designed to protect the user's fingers FROM contact with contaminated surfaces. The present invention prevents transmission of microbes from the user's fingers TO a surface. The Oradini device is designed for multiple untrained users in public places like bathrooms and is mounted permanently in such locations. Repeated improper use in this way amplifies the risk of dispensing a contaminated cover. Additionally, the annular membrane described by Oradini, designed to prevent dispensing multiple tubular covers, is a potential source for contamination upon withdrawal from the device, since it may come in contact with the fingers of multiple untrained individuals. There is also a risk of contaminating the stacked covers within the dispenser by aerosolized particles, since it is repeatedly accessed. As such, even clean, boxed, disposable gloves have been documented to become contaminated over time in various environments, such as operating suites, kitchens, bathrooms and restaurants. There is no disclosed method of maintaining a sanitized cover within the device.

By contrast, the novel design of the present invention finger cover system sanitizes the covers immediately prior to use, providing a freshly sanitized cover. The device can be utilized, cared for and cleaned by a single individual who is skilled in its use. It is portable and may be easily carried by the user to different locations of use, such as at a table at a restaurant.

The tubular shape, size and appearance of Oradini's covers are over-complicated with respect to the present invention. The Oradini covers may inhibit facile usage of the fingers while serving food and possibly decrease grip on a surface, such as a plate. The novel design of the finger cover in the present invention improves adhesion to the surface of the plate. Finally, the Oradini finger covers require either an adhesive or complex surface textures in order to dispense the covers individually. An embodiment of the present invention finger cover requires no adhesive, attaching to the finger using a novel press-fit design. Additionally, individual covers are easily dispensed without need for textured interior and exterior surfaces as in the Oradini device.

U.S. Pat. No. 9,723,879 to Delgrosso also describes tubular finger sheaths, which maintain their sanitary state by impregnation with antimicrobial agents. Such agents have the disadvantage of creating an unwanted exposure of the food surface to the antimicrobials, potentially causing an allergic reaction. There is an unnecessary expense attendant to antimicrobial application. There is also a negative environmental impact upon disposal, potentially causing multiple drug resistant microbial strains at the site of disposal, such as a landfill.

U.S. Published Application No. US 2008/0000011 A1 to Ayala discloses a sanitary finger cover made from flexible material, preferably plastic, in the shape of a pocket. Neither a method of dispensing the cover nor any means of maintaining the cover sanitary is disclosed.

U.S. Published Application No. US 2013/0025016 A1 to Koffi et al. (Koffi) discloses fingertip covers made from various materials, which allow control of touch screen electronics. The primary purpose is to prevent contamination of the user's fingers. The tips adhere to each finger with adhesive and require a backing strip to be removed with a second hand. No sanitary aspect is disclosed.

The prior art discussed above fails to describe devices or methods of dispensing sanitary finger covers which meet the requirements of being sanitized on demand, are inexpensive, inconspicuous, portable, rapidly applied with one finger using a non-slip material, and which may be disposable and biodegradable.

SUMMARY OF THE INVENTION

The present invention relates to sanitary finger covers and embodiments of a dispenser to dispense them. The present invention includes the following interrelated objects, aspects and features:

(1) The finger covers have been sanitized on demand prior to application by the user. The finger covers can be rapidly and easily applied using a single finger. The finger covers are sized to completely cover the entire contact surface of the finger, including the pad, sides and tip of the distal phalanx.

(2) The fingernail surface may remain uncovered since it poses low risk of contact with the food-containing surface. However, a cover which encloses the entire fingertip may be utilized.

(3) Sanitization occurs through several possible sanitizing methods, including exposure to ultraviolet light at disinfecting wavelengths, generally in the range between 250-300 microns. This is achieved using a battery-operated ultraviolet LED housed within the device. Different wavelengths of ultraviolet light may be provided depending on the application. Ultraviolet LED systems are available from multiple vendors and are readily customizable.

(4) Once the sanitized finger cover is applied to the tip of the finger, the user can then immediately grasp a food-containing surface without risk of transmitting contaminants and infectious agents.

(5) The dispenser is lightweight and can be easily carried or attached to the user with a strap, clip or an adhesive, such as hook and pile fastening means sold under the registered trademark VELCRO®. Finger covers may be replaced in the dispenser as they are depleted, in some embodiments using a cartridge filled with pre-sanitized covers or individually.

(6) Summarizing, several novel features and advantages are apparent from the detailed description of the present invention in the specific description of the preferred embodiments. These include dispensing finger covers, which are sanitized on demand, ensuring a freshly sanitized finger cover immediately prior to use. This also prevents dispensing a pre-sanitized finger cover, which may have been inadvertently contaminated within a multi-use dispenser. This also avoids the likelihood of recontamination as with a continuously gloved hand.

(7) The finger covers are fashioned from inexpensive materials, which may be disposable, biodegradable and in some embodiments, reusable. The sanitized surfaces of the finger covers may be fashioned to improve contact between the finger and plate surface to prevent slippage. The method of application is rapid and can utilize a single finger, increasing compliance and decreasing the likelihood of contamination during application. Removal is similarly quick and easy. The overall cost of using the device per customer is minimal.

Accordingly, it is a first object of the present invention to provide sanitary finger covers and a dispenser to dispense them.

It is a further object of the present invention to provide such an invention in which the dispenser can dispense the finger covers using only a single finger of the user.

It is a further object of the present invention to provide such finger covers with a surface texture designed to prevent slippage between the finger and an object engaged by the finger.

It is a still further object of the present invention to provide a dispenser which dispenses finger covers which are sanitized just before dispensing.

It is a still further object of the present invention to provide such a dispenser which can serially dispense multiple finger covers one at a time.

It is a still further object of the present invention to provide finger covers which expandably fit various finger sizes and shapes through its novel design.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
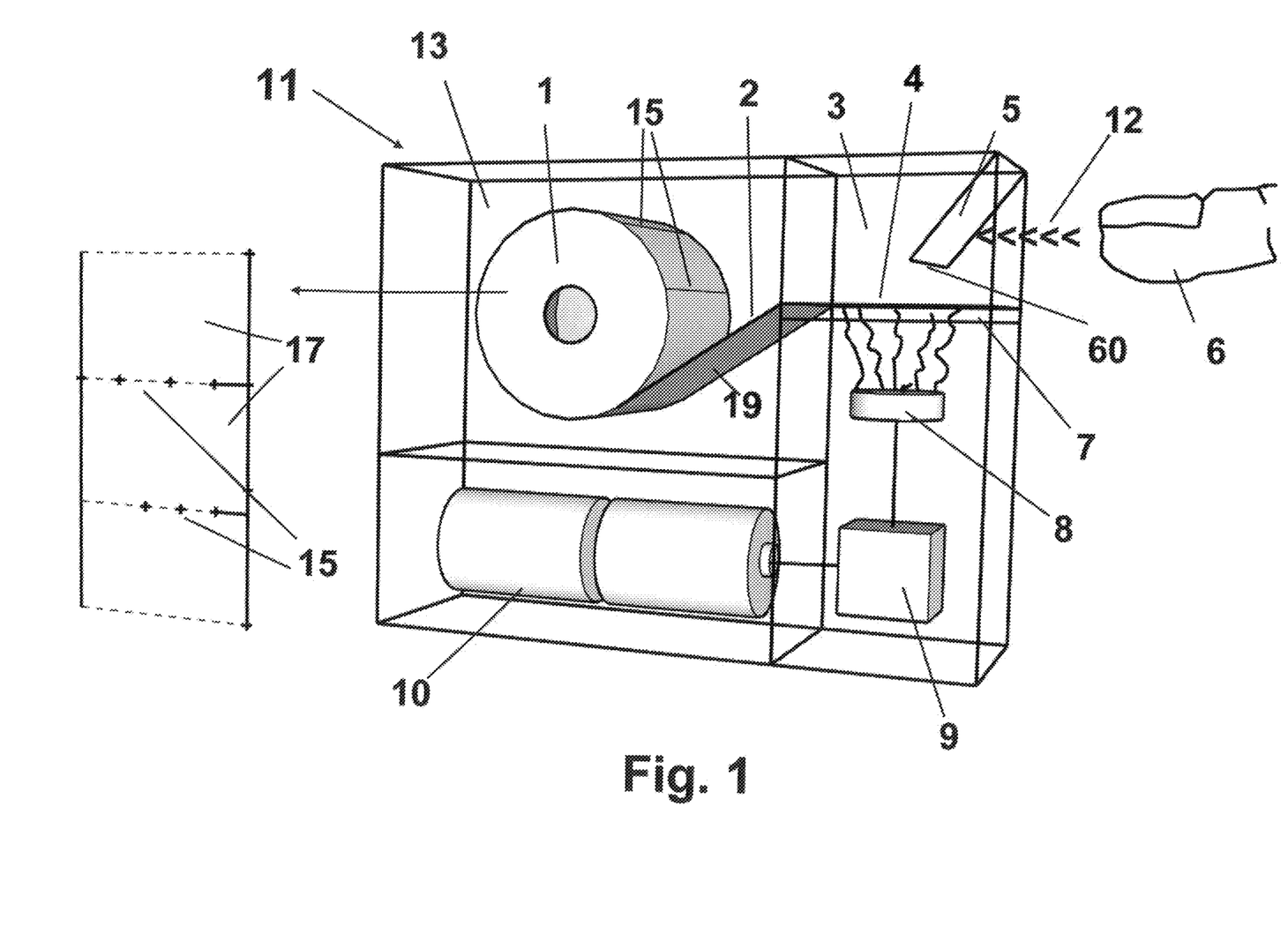
FIG. 1 shows a side view of the dispensing device constructed in accordance with the invention, with the user's finger about to be inserted into the finger chamber in the direction of the arrowheads.

With reference first to FIG. 1, a view of a first embodiment of the dispensing device is shown generally designated by the reference numeral 11 with the user's finger 6 being inserted into the finger chamber 3 in the direction of the arrowheads 12. The hinged chamber door 5 is shown in the partially open position. The roll of tape material 1 is shown providing a continuous sheet of tape material extending diagonally upward 2 onto the translucent floor 7 of the finger chamber 3. The roll of tape material is housed in a separate compartment 13 from the finger chamber 3 so that the inserted finger 6 does not come in contact with the roll of tape. Preformed perforations or tear-lines 15 in the tape material allow for easy separation of finger-sized segments 17.

The continuous piece of tape material 1, 2, 4 is pulled into the finger chamber 3 with the adhesive surface of the tape material facing upwards. The non-adhesive surface 19 of the tape material rests on the translucent floor 7 of the finger chamber 3. The ultraviolet LED 8 shines ultraviolet light through the translucent floor 7 of the finger chamber 3 (indicated by the vertical jagged lines above the LED) onto the non-adhesive surface of the tape material resting on the translucent floor 7.

Preferably, the entire assembly is opaque, except for the translucent floor 7 of the finger chamber 3, so that ultraviolet light is not visible outside the device. The batteries 10 provide optimal electrical power to the ultraviolet LED 8 utilizing a constant-current regulator 9. The constant-current regulator 9 also triggers operation of the ultraviolet LED 8 and regulates exposure time of the ultraviolet LED light to the contact surface of the tape material. The user can turn on the ultraviolet LED automatically or manually with each use using a switch (not shown).

Figure 2:
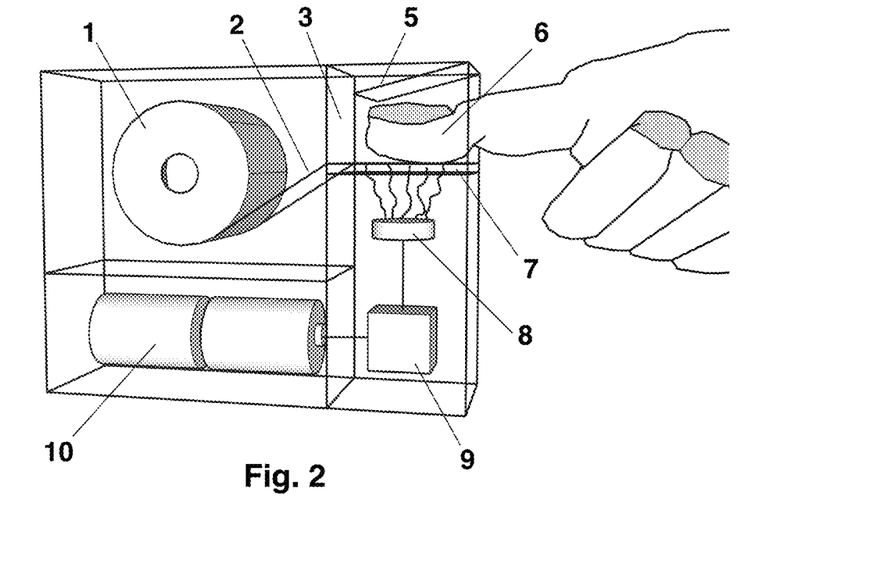
FIG. 2 shows the same side view of the dispenser of FIG. 1 with the user's finger pressing down upon the adhesive surface of the sanitized tape material on the translucent floor of the finger chamber above the ultraviolet LED.

FIG. 0.2 shows the finger 6 within the finger chamber 3, pushing open the hinged door 5. The finger 6 is shown pressing down on the adhesive surface of the tape material on the translucent floor 7 of the finger chamber 3. The translucent floor 7 may be flat or concave to conform to the shape of the pad of the finger, thus facilitating application of the tape material along the tip, sides and pad of the finger. The translucent floor 7 may be made from any translucent material that allows effective transmission of ultraviolet light, such as quartz.

Figure 3:
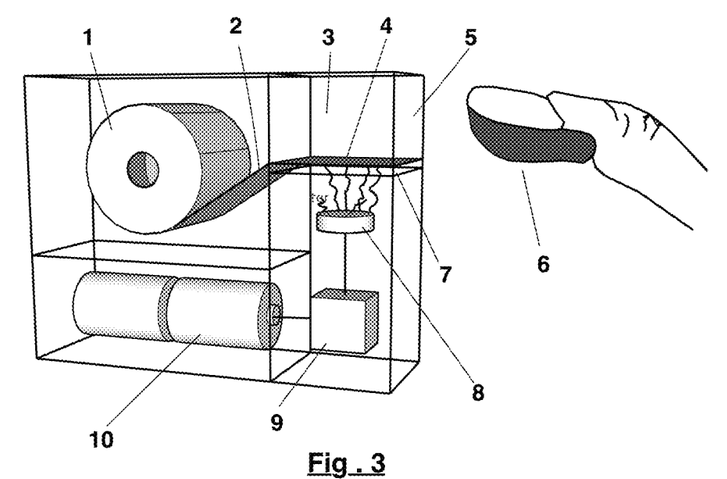
FIG. 3 shows the same side view of the dispenser of FIG. 1 with the finger removed from the finger chamber of the dispenser with the segment of sanitized tape material applied.

FIG. 3 shows the finger 6 removed from the finger chamber 3 with the tape material segment 17 adherent to the tip, sides and pad of the finger 6. The hinged door of the finger chamber has closed 5, causing separation of the tape segment 17 (see FIG. 1) along the preformed perforations 15 in the roll of tape material 1. A new segment 17 of tape material 1, with the adhesive surface facing upward, has been pulled into the finger chamber 3 onto the translucent floor 7. This occurs during removal of the finger with attached tape material prior to separation. Closure of the finger chamber door 5 automatically turns on the ultraviolet LED, which may also be controlled manually with an on/off switch (not shown).

Figure 4:
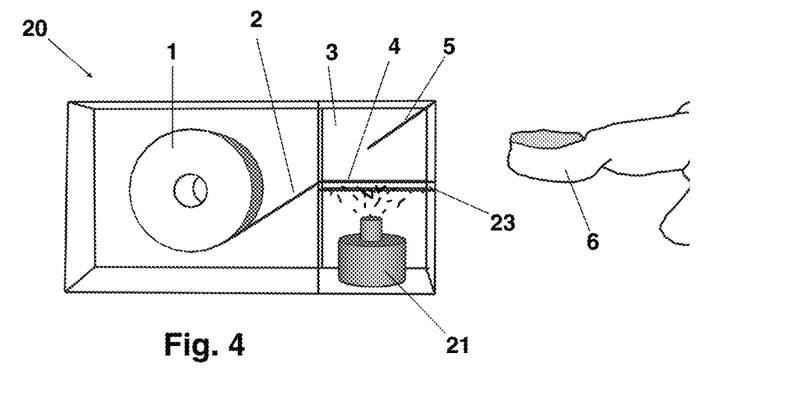
FIG. 4 shows an alternative embodiment of the inventive dispenser in which the ultraviolet LED and battery compartments are replaced with a spray disinfectant canister and the translucent floor is replaced with a screen floor to allow adequate spray penetration.

FIG. 4 shows another embodiment of a dispenser 20, which uses a spray canister 21 to apply a sanitizing agent, such as hydrogen peroxide, to the non-adhesive surface of the tape material. The tape material rests on a screen floor 23 of the finger chamber 3. The screen floor 23 allows the sanitizing agent to pass through onto the non-adhesive surface of the tape material. The canister may activate through sensing of the finger 6 entering the chamber 3, by, for example, a photoelectric eye (not shown).

Figure 5:
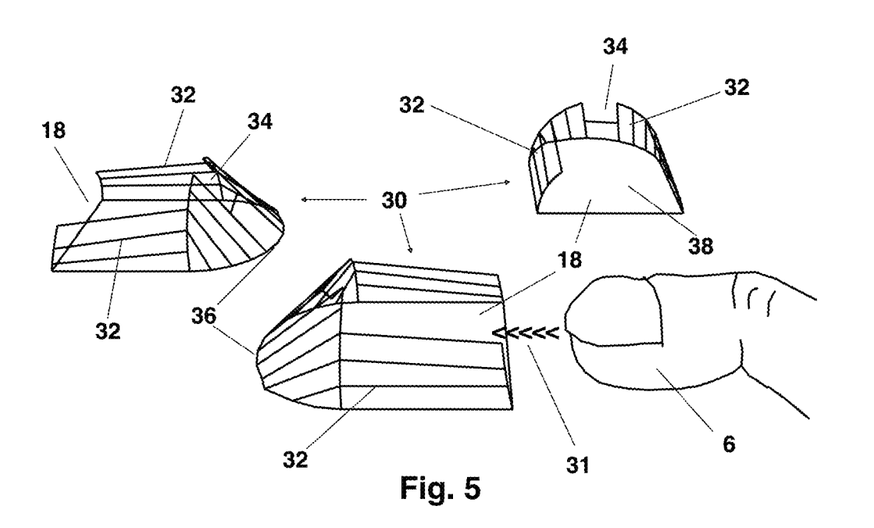
FIG. 5 shows an alternative embodiment of the finger covers utilizing preformed "finger slippers."

FIG. 5 shows multiple views of another embodiment of individual "Finger Slippers" 30. The finger 6 is shown being inserted into the rear opening 18 of the finger slipper 30 in the direction of the arrowheads 31. The finger slipper has a nose 36 and a bottom wall 38. The finger slippers can be made from a variety of inexpensive materials such as pulp paper, cardboard, rubber or plastic. This material may be recyclable, biodegradable, disposable or reusable, flexible, expandable, non-absorbent and/or impervious to liquids or microbial agents. Some materials may be clear for inconspicuous usage. The under surface may be fashioned to be flat or with a textured surface to improve grip by the user. The sides of the finger slippers 30 comprise expandable side panels 32 and are slanted inwards and expand outwards as the finger is inserted. This novel design creates a tight fit around the finger and avoids the need for an adhesive inner coating. However, an adhesive inner coating may be utilized. Similarly, the tip of the finger slipper 30 has a novel means of expansion in that the expandable side panels 32 have accordion-like pleats and widen to receive the fingertip and improves the fit for multiple finger sizes. In the preferred embodiment, the finger slipper has an open top defining a slot 34 which can change dimensions as expandable side panels 32 expand or contract. The slot allows the nail of a finger received within the finger slipper 30 to remain exposed. As shown in FIG. 5, the slot 34 terminates just proximal of the nose 36. In use, the finger slipper is sanitized with ultraviolet light or a sanitizing liquid either sprayed or otherwise coated thereon.

Figure 6:
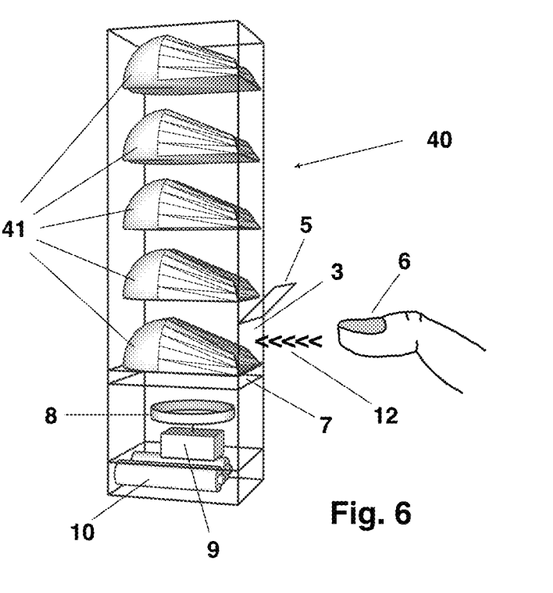
FIG. 6 shows an alternative embodiment of the dispensing device which utilizes a plurality of the finger slippers as shown in FIG. 5 in a stacked arrangement within the device.

FIG. 6 shows a further embodiment 40 of the dispensing device, in which the finger slippers 41 are stacked within the dispensing device 40. The finger slippers descend by gravity or other means into the finger chamber 3 for exposure to the ultraviolet LED 8 through the translucent floor 7 of the finger chamber 3. The lid 5 of the finger chamber 3 is shown in partially open position to reveal the newly sanitized finger slipper 41. The finger 6 is shown inserting in the direction of the arrowheads 12 into the sanitized finger slipper. Once applied to the finger and removed from the finger chamber, a new finger slipper 41 descends into the finger chamber 3. The lid 5 then closes and triggers operation of the ultraviolet LED 8. The LED constant-current regulator 9 maintains the appropriate electrical current for optimal function of the ultraviolet LED 8 delivered from the batteries 10. The LED constant-current regulator also regulates the duration of time the ultraviolet LED 8 is operational between cycles. The ultraviolet LED 8 can also be manually turned on if so required. All surfaces of the dispensing device are opaque, with the exception of the translucent floor 7 of the finger chamber. This is to avoid exposure of ultraviolet light outside the device.

Figure 7:
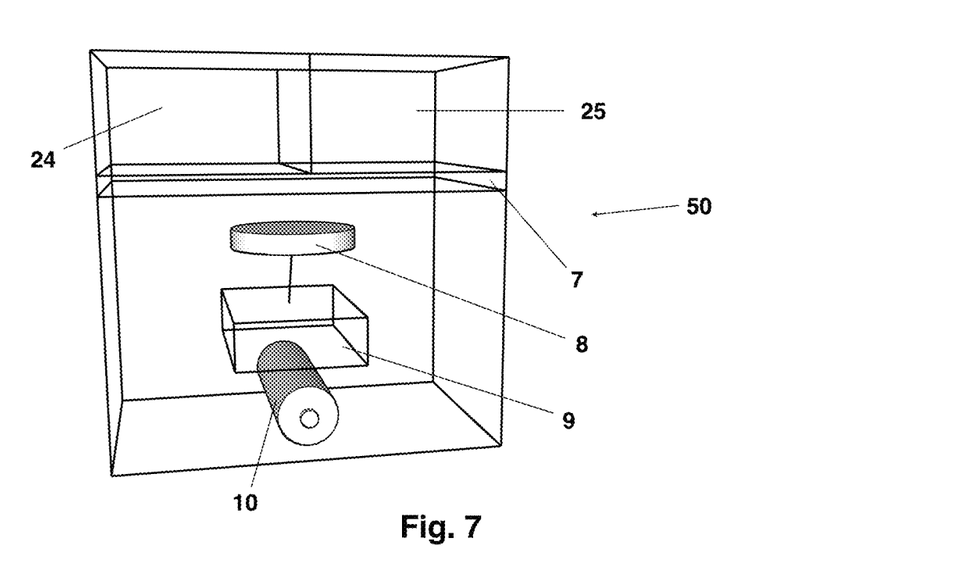
FIG. 7 shows an alternative embodiment of the inventive dispenser in which two REUSABLE finger slippers (not shown) can be placed into the indicated finger chambers between uses for exposure to the ultraviolet LED.

FIG. 7 shows another embodiment of dispenser 50 in which two REUSABLE finger slippers (not shown) are placed in the finger chambers 24, 25 between uses. The reusable finger slippers are exposed to the ultraviolet LED 8 in a similar fashion to the disposable tape application in FIG. 1 and the finger slipper application in FIG. 6. Two finger slippers are utilized to ensure immediate availability of at least one finger slipper, while the ultraviolet LED 8 is sanitizing the other finger slipper. The roll of tape 1 may or may not be utilized, providing an additional layer of protection over the contact surface of the reusable finger slipper.

Operation of the embodiments of the present invention is as follows.

In the embodiment 11 of FIGS. 1-3, the user's finger 6 is inserted into the finger chamber 3 by pushing against the hinged chamber door 5. Once inside the finger chamber, the finger presses down onto the adhesive surface of the tape material 1, which rests on the translucent floor 7. The translucent floor may be flat or concave to match the contour of the finger, facilitating contact between the finger pad, sides and tip and the adhesive surface of the tape material. The finger is then withdrawn with the tape material attached, pulling a new segment of tape material into the finger chamber. The segment 17 on the finger is torn from the roll at the tear line 15. The finger chamber door closes and facilitates tearing away of the segment 17 of tape on the finger. The size of the segment of tape 17 is determined by the perforations, or tear lines 15, in the roll of tape material. Rolls of tape material with a variety of predetermined perforated segment lengths and widths may be provided to allow for different finger sizes and shapes. Alternative embodiments may contain non-perforated, continuous rolls of tape material, which may be torn off onto the finger by a sharp lower edge 60 of the finger chamber door (FIG. 1). A new segment of tape material is then pulled into the finger chamber by withdrawing the finger from the finger chamber with the attached segment of tape material. The non-adhesive surface of the newly advanced segment of tape material rests on the translucent floor of the finger chamber. As the finger is withdrawn, the finger chamber door closes, triggering operation of the ultraviolet LED 8, sanitizing the new segment of tape material. Ultraviolet light is emitted from the LED 8 at disinfecting wavelengths, generally between 255-270 microns. Ultraviolet LEDs of differing wavelengths may be provided depending on the application. The ultraviolet LED 8 remains operational for an appropriate period of time to complete effective sanitization, controlled by the constant-current regulator. The ultraviolet LED 8 may also be turned on manually in certain applications. The ultraviolet LED 8 light shines through the translucent floor 7 of the finger chamber 3 onto the non-adhesive surface of tape material 1. The close proximity of the emitted UV light to the non-adhesive surface of the tape material effectively sanitizes the tape material at short exposure times. The composition of the floor of the chamber is made from any translucent material, such as quartz, which allows for an effective, sanitizing intensity of the ultraviolet light to penetrate the floor. The contact-surface of the inner-segments of tape material within the roll of tape is not exposed to air until dispensed and remain clean until sanitized by the LED 8. When depleted, the rolls of tape may be provided pre-sanitized in a cartridge for easy insertion into the dispenser. A tape-containing cartridge is designed to prevent contact of the user's finger with the roll of tape. The only opening of the cartridge is a thin sliver large enough to allow the advancing edge of tape to be pulled into the finger chamber. Since the interior layers of tape are not exposed to air, the sanitary condition of the roll is maintained. In some applications, this sanitary level may be sufficient to not require additional sanitization by the ultraviolet LED 8, or other means, prior to dispensing the cover.

In another embodiment 40 of FIG. 6, the dispensing device utilizes individual "Finger Slippers" 41. The finger slippers 41 are sanitized using ultraviolet LED light as previously described. A plurality of the finger slippers 41 are contained within the dispenser, preferably in a stacked arrangement, allowing for easy advancement into the finger chamber by gravity. Alternatively, a spring mechanism (not shown) may be utilized. Adjacent finger slippers 41 may be attached in such a way as to pull a new finger slipper into the finger chamber whenever the user removes a finger slipper. The attachable segment may then be detached with each new application by the user. The finger slipper 41 may be applied to the finger 6 by inserting the finger into the open back of the finger slipper and sliding the finger forward into the tip of the finger slipper as shown in FIG. 5. The novel design of the finger slipper 41 provides expansion around the finger as the finger is inserted, using expandable side panels and an expansion slot 34 in the tip. This creates a tight fit with a variety of finger sizes without the need for adhesive. This design also avoids limitation of movement across the finger joint since it is sized to fit only the distal phalanx of the finger. An alternative embodiment provides an adhesive material inside the finger slipper similar to the tape material embodiment. The finger slippers may be provided in a variety of shapes and sizes. The finger slippers may be made from a variety of materials such as paper or pulp cardboard and may be disposable, recyclable, reusable, porous or impervious to viruses, bacteria and other microbial agents. Similar to the tape material embodiment of FIGS. 1-3, the sanitized surface of the finger slipper may be fashioned to improve the grip on a surface and prevent slippage. A plurality of pre-sanitized finger slippers may be provided in a cartridge for easy replacement into the dispenser.

In another embodiment 50 of FIG. 7, a reusable finger slipper (not shown in FIG. 7) is utilized. The user inserts the reusable finger slipper into the indicated finger chamber 24 or 25 after each use, where it is stored between uses. Visible contaminants may be removed from the reusable finger slipper by the user before reinsertion into the finger chamber for repeat sanitization. While inside the finger chamber, it is exposed to the ultraviolet LED in a similar fashion to the finger tape material of the embodiment of FIG. 1, and the finger slipper embodiment of FIG. 6. The user then reinserts their finger into the newly sanitized finger slipper and withdraws it for immediate use. Alternatively, a second reusable finger slipper may be available in an adjacent chamber to avoid time delays between sanitization. The reusable finger slipper can be fashioned in a variety of shapes, which allow for easy finger insertion and withdrawal. The reusable finger slippers may be made from a variety of materials, which permit rapid sanitization using ultraviolet light while retaining mechanical stability during repeated use. In an alternative embodiment, the sanitized tape material 1 of FIG. 1 may be applied to the reusable finger slipper as well to provide an additional layer of protection.

While the above description contains many specificities, these should not be construed as limitations on the scope, but rather as an exemplification of several embodiments thereof. Many other variations are possible. For example, while the thumb is the most frequent finger in contact with a surface containing food, any finger on either hand can utilize this system. In another embodiment, the finger slippers are stacked in a circular housing similar to a Ferris Wheel, with the ultraviolet LED in a central location. Each individual finger slipper is oriented with the contact surface towards the central ultraviolet LED. This will sanitize multiple covers simultaneously for rapid application to multiple fingers when needed.

As such, an invention has been disclosed in terms of preferred embodiments thereof, which fulfill each and every one of the objects of the invention as set forth hereinabove, and provide a new and useful sanitary finger covers and dispenser of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:
1. An article dispenser for dispensing sanitary finger covers, comprising:
 a) a housing containing at least one finger cover;
 b) a chamber in said housing sized to receive a finger of a user, said chamber also receiving a finger cover and having a surface supporting a finger cover within said chamber, said surface being on a floor of said chamber made of a material permitting light transmission therethrough; and
 c) means for sanitizing said finger cover received within said chamber;
 d) whereby said user can move a user's finger into said chamber and subsequently remove said finger from said chamber with a sanitized finger cover attached to said finger.

2. The article dispenser of claim 1, wherein said at least one finger cover comprises a roll of plural finger covers, said finger covers being conveyed to said chamber.

3. The article dispenser of claim 2, wherein adjacent ones of said finger covers are separable by perforations.

4. The article dispenser of claim 2, wherein said roll of plural finger covers is located in a compartment in said housing, an opening connecting said compartment with said chamber whereby a series of finger covers can be serially conveyed to said chamber from said compartment.

5. The article dispenser of claim 1, wherein said means for sanitizing said finger cover comprises a source of ultraviolet light below said floor, whereby when said source of ultraviolet light is activated, said light shines through said floor and sanitizes a finger cover on said surface.

6. The article dispenser of claim 5, further including an electrical power supply within said housing which, when activated, activates said source of ultraviolet light.

7. The article dispenser of claim 6, wherein said electrical power supply comprises at least one battery.

8. The article dispenser of claim 1, wherein said floor comprises a screen with perforations therethrough.

9. The article dispenser of claim 8, wherein said means for sanitizing said finger cover comprises a source of a sanitizing spray located below said screen, which when activated sprays a sanitizing solution through said screen and onto a finger cover on said surface.

10. The article dispenser of claim 1, whereby a finger cover is attached to said user's finger by virtue of adhesive coated on said finger cover.

11. The article dispenser of claim 1, wherein said at least one finger cover comprises plural finger covers vertically stacked in a compartment adjacent said chamber, said finger covers being supplied one at a time to said chamber.

12. The article dispenser of claim 1, wherein said at least one finger cover comprises plural finger covers vertically stacked in a compartment adjacent said chamber, said finger covers being supplied one at a time to said chamber.

\* \* \* \* \*